US 11,071,516 B2

(12) United States Patent
Torp et al.

(10) Patent No.: US 11,071,516 B2
(45) Date of Patent: Jul. 27, 2021

(54) ENHANCED-RESOLUTION ULTRASOUND IMAGING OF FLUID PATHS

(71) Applicant: Norwegian University of Science and Technology (NTNU), Trondheim (NO)

(72) Inventors: Hans Torp, Trondheim (NO); Lasse Lovstakken, Trondheim (NO)

(73) Assignee: Norwegian University of Science and Technology (NTNU), Trondheim (NO)

( * ) Notice: Subject to any disclaimer, the term of this patent is extended or adjusted under 35 U.S.C. 154(b) by 365 days.

(21) Appl. No.: 16/329,568

(22) PCT Filed: Sep. 1, 2017

(86) PCT No.: PCT/GB2017/052553
§ 371 (c)(1),
(2) Date: Feb. 28, 2019

(87) PCT Pub. No.: WO2018/042191
PCT Pub. Date: Mar. 8, 2018

(65) Prior Publication Data
US 2019/0223828 A1 Jul. 25, 2019

(30) Foreign Application Priority Data
Sep. 2, 2016 (GB) .................................... 1614950

(51) Int. Cl.
*A61B 8/06* (2006.01)
*A61B 8/14* (2006.01)
*A61B 8/08* (2006.01)

(52) U.S. Cl.
CPC .............. *A61B 8/06* (2013.01); *A61B 8/0891* (2013.01); *A61B 8/14* (2013.01); *A61B 8/488* (2013.01);
(Continued)

(58) Field of Classification Search
CPC ........... A61B 8/06; A61B 8/14; A61B 8/0891; A61B 8/488; A61B 8/5207; A61B 8/5253; A61B 8/5269; A61B 8/481
See application file for complete search history.

(56) References Cited

U.S. PATENT DOCUMENTS 6,277,075 B1 8/2001 Torp et al.
6,527,720 B1 3/2003 Ustuner et al.
(Continued)

FOREIGN PATENT DOCUMENTS

WO 2013150917 10/2013
WO 2015133677 9/2015

OTHER PUBLICATIONS

Errico, C. et al., "Ultrafast ultrasound localization microscopy for deep super-resolution vascular imaging", Nature, vol. 527, pp. 499-502, Nov. 2015.

*Primary Examiner* — Boniface N Nganga
(74) *Attorney, Agent, or Firm* — Diederiks & Whitelaw, PLC.

(57) ABSTRACT

An ultrasound imaging method in which ultrasound signals are transmitted into a living organism, reflected from fluid flowing along a path within the organism, and received by an ultrasound transceiver system with a resolution limit in a first direction. These signals are used to generate data representing a sequence of images over time; each image including a speckle pattern arising from interference within the reflected ultrasound signals. A peak-sharpening operation is applied to the image data, generating data representing a sequence of resolution-enhanced images, each having a resolution in the first direction finer than the resolution limit of the transceiver system in that direction, and including a respective peak-sharpened speckle pattern. A combining operation is applied to generate data representing an output image in which the path of the fluid is represented by
(Continued)

a superimposition of the peak-sharpened speckle patterns from the resolution-enhanced images.

21 Claims, 8 Drawing Sheets

(52) U.S. Cl.
CPC .......... *A61B 8/5207* (2013.01); *A61B 8/5253* (2013.01); *A61B 8/5269* (2013.01); *A61B 8/481* (2013.01)

(56) References Cited

U.S. PATENT DOCUMENTS

| | | | |
|---|---|---|---|
| 9,734,602 B2 | 8/2017 | Park et al. | |
| 2003/0149357 A1 | 8/2003 | Liu | |
| 2007/0083114 A1 | 4/2007 | Yang et al. | |
| 2015/0289847 A1* | 10/2015 | Park | G01S 7/52077 |
| | | | 600/443 |
| 2016/0173770 A1 | 6/2016 | Fosodeder et al. | |

* cited by examiner

ENHANCED-RESOLUTION ULTRASOUND IMAGING OF FLUID PATHS

CROSS-REFERENCE TO RELATED APPLICATIONS

This application represents the U.S. National Phase of International Application No. PCT/GB2017/052553 entitled "Enhanced-Resolution Ultrasound Imaging of Fluid Paths" filed 1 Sep. 2017, which claims priority from United Kingdom Patent Application No. 1614950.2 filed on 2 Sep. 2016. The entire contents of these applications are incorporated herein by reference.

BACKGROUND OF THE INVENTION

This invention relates to methods and apparatus for imaging fluid paths using ultrasound signals.

It is known from the field of medical ultrasonography to generate images of veins and arteries, carrying blood, using two-dimensional B-mode images. Doppler processing can additionally be used to determine information about the velocity of blood flow within these vessels.

However, the resolution of ultrasound scanning is limited both axially and laterally, which makes it difficult or impossible to view smaller fluid paths, such as cerebral microvessels, using conventional techniques. Laterally, the resolution is limited by the diffraction of the ultrasound waves, being equal to $f\#\times\lambda$, where $f\#$ is the ratio of depth and the transducer aperture (which is typically in the range 1 to 5), and where $\lambda$ is the transmission wavelength. The choice of transmission frequency represents a balance between increased penetration depth and increased lateral resolution. Signals from a typical 8 MHz ultrasound scanner have a wavelength, $\lambda$, of around 0.2 mm in human tissue, resulting in a lateral resolution of around a millimetre, at depths of up to a few centimetres. Transmitting ultrasound frequencies at higher frequencies (e.g., 40 MHz or above) can improve the resolution (e.g., to around 0.1 mm), but reduces the imaging depth (e.g., to just a few millimetres). Axial resolution is limited by the pulse length, being equal to $0.5\times N_c \times \lambda$, where $N_c$ is the number of cycles in a transmitted pulse (typically in the range 2 to 10), and $\lambda$ is the wavelength. Shorter pulses give increased (finer) axial resolution, but do not penetrate as deeply, because they require higher bandwidth in the receiver, which increases the thermal noise level.

Microvessels may have diameters of less than ten micrometres. To image blood vessels on a sub-millimetre level, but more than ten millimetres below the tissue surface, it is typically necessary to use a super-resolution imaging technique, which can generate images having a lateral and/or axial resolution that is finer than the inherent limits of the ultrasound transceiver system. One such method is described in the paper "Ultrafast ultrasound localization microscopy for deep super-resolution vascular imaging" by Errico et al., Nature 527, 499-502 (26 Nov. 2015). This involves injecting an ultrasound contrast agent into the blood stream, consisting of gas microbubbles a few micrometres in diameter, and using ultrafast B-mode imaging to detect single echoes from individual microbubbles. A series of 75,000 separate image frames may be acquired over an extended period, such as 150 seconds or ten minutes. The microbubbles are smaller than the diffraction limit of the ultrasound transceiver system, and are treated as point scatterers. By making use of the (known) point-spread function, coordinates for the centroid of each microbubble can be calculated from each image, at a lateral resolution beyond the diffraction limit of the ultrasound system. A microbubble density map can then be generated by combining the coordinate data from across the series of image frames. This density map reveals the underlying microvessel structure. Individual microbubbles can also be tracked across frames to calculate in-plane velocity vectors.

However, the substantial periods of time required to obtain such images makes such a technique unsuitable for use on moving subjects, such as conscious people or animals, because any movement of the subject or the ultrasound transducers during the imaging process will lead to a poor quality output. Moreover, injecting a contrast agent is time-consuming, and requires a skilled clinician or technician to do it safely. Injections also present an infection risk and can be traumatic to patients.

The present invention seeks to provide a faster approach to generating enhanced-resolution images.

SUMMARY OF THE INVENTION

From a first aspect, the invention provides an ultrasound imaging method comprising:
transmitting ultrasound signals into a living organism;
receiving reflected ultrasound signals from fluid that is flowing along a path within the living organism with an ultrasound transceiver system that has a resolution limit in a first direction;
using the received ultrasound signals to generate data representing a sequence of images over time, each image including a speckle pattern arising from interference within the ultrasound signals reflected from the fluid that is flowing along the path;
applying a peak-sharpening operation to the image data, to generate data representing a sequence of resolution-enhanced images, each resolution-enhanced image having a resolution in said first direction that is finer than the resolution limit of the ultrasound transceiver system in said first direction, and including a respective peak-sharpened speckle pattern; and
applying a combining operation to the data representing the sequence of resolution-enhanced images to generate data representing an output image in which the path of the fluid is represented by a superimposition of the peak-sharpened speckle patterns from the sequence of resolution-enhanced images.

From a second aspect, the invention provides an ultrasound imaging system comprising:
an input for receiving data from an ultrasound transceiver system, the data representing a sequence of images over time having a maximum resolution in a first direction, each image including a speckle pattern arising from interference within ultrasound signals reflected from fluid that is flowing along a path within a living organism; and
a processing subsystem configured to:
apply a peak-sharpening operation to the image data, to generate data representing a sequence of resolution-enhanced images, each resolution-enhanced image having a resolution in said first direction that is finer than said maximum resolution in said first direction, and including a respective peak-sharpened speckle-pattern; and
apply a combining operation to the data representing the sequence of resolution-enhanced images to generate data representing an output image in which the fluid path is represented by a superimposition of the peak-sharpened speckle-patterns from the sequence of resolution-enhanced images.

Thus it will be seen by those skilled in the art that, in accordance with the invention, speckle patterns from fluid moving within the living organism are sharpened with a peak-sharpening operation that enhances their effective resolution, and are superimposed across multiple image frames. It is thereby possible to generate an output image showing the fluid path at a resolution (in at least one direction) that can be finer than the resolution limit (in that direction) of the ultrasound transceiver system that generated the data. This enhanced-resolution imaging can be carried out much more quickly than the prior approach described above, using a much shorter sequences of images. It can even potentially be carried out in real-time, to generate live video. It also does not require a contrast agent to be injected into the organism (although this is not excluded).

The living organism may be a person, an animal, a plant or any other organism. In a preferred set of embodiments it is an adult or infant human. The fluid may comprise any liquid or gas. The fluid preferably comprises regions of different densities. The fluid may comprise one or more gas or liquid bubbles or solid particles in a medium, where the bubbles or particles have a first density or mean density and the medium has a second, different density or mean density. In this way, the fluid is likely to give a characteristic speckle pattern when illuminated by ultrasonic waves. In preferred embodiments, the fluid is blood. The way that ultrasound reflects off blood cells in blood can give blood a characteristic speckle pattern when imaged using ultrasound.

Although, in preferred embodiments, the fluid is only blood (i.e., not containing any contrast agents), in some embodiments, the fluid (e.g., blood) may comprise an ultrasound contrast agent such as microbubbles or particles—e.g., injected by a medical practitioner. Use of a contrast agent can increase the signal-to-noise ratio for blood signals. This can avoid the need for high-pass clutter filtering for attenuating signal from surrounding tissue, since this may be done instead by exploiting the non-linear scattering characteristics of the microbubbles. This is particularly advantageous when imaging very small blood vessels where echoes are weak.

The path of the fluid may be unconstrained—e.g., turbulent flow within a larger region of fluid—but it is preferably constrained by a vessel, such as blood vessel. In this way, imaging the path of the fluid can be equivalent to imaging the internal bore of the vessel itself. If the wall thickness of the vessel is negligible, then imaging the fluid path can be equivalent to imaging the vessel itself.

The data representing an output image may be stored in a memory, or it may be displayed to a user—e.g., on an electronic display or a paper print-out.

In some embodiments, the input in the ultrasound imaging system comprises a port, such as a USB, WiFi or Ethernet connection, for receiving the data representing the sequence of images (e.g., from a separate ultrasonography unit). In other embodiments, the ultrasound imaging system comprises an ultrasound transceiver system, having a resolution limit in said first direction, for a particular set of ultrasound signals (e.g., having a particular frequency and/or duration), the resolution limit preferably being equal to said maximum resolution.

A resolution limit of the ultrasound transceiver system may be specific to a particular configuration of the ultrasound transceiver system. It may, for instance, depend on the frequency and/or duration of the transmitted ultrasound signals. These parameters may be variable—e.g., user-configurable.

The resolution limit may be an axial or longitudinal limit, or it may be an angular or lateral limit. It may be a diffraction limit of the transceiver system, for the transmitted ultrasound signals. The enhanced-resolution imaging may be super-resolution imaging. The resolution limit may be determined in Cartesian coordinates (e.g., a rectilinear width or height, after a scan conversion step), but is preferably determined in an inherent coordinate system of the ultrasound transceiver system (e.g., angular or axial distance, before any scan conversion). It will be appreciated that references herein to the resolution limit of an ultrasound imaging system can apply equally to the maximum resolution of data received from an ultrasound transceiver system by the ultrasound imaging system.

In some embodiments, the ultrasound transceiver system may have two resolution limits in different respective directions (e.g., an axial resolution limit and an angular resolution limit), which may differ from each other. In this case, each resolution-enhanced image preferably also has a second resolution in a second direction (different from the first direction) that is finer than a second resolution limit of the transceiver system in said second direction.

In some embodiments, the peak-sharpening operation increases the resolution of the image data perpendicularly to the path of the fluid, within an imaging plane. Unless the fluid path runs entirely axially or entirely laterally within the image plane, such an operation will thereby increase the resolution in both the axial direction and the lateral direction.

In some embodiments, the ultrasound transceiver system may generate three-dimensional image data. The peak-sharpening operation may be applied to three-dimensional image data, to generate data representing a sequence of 3D resolution-enhanced images, each 3D resolution-enhanced image having a resolution in said first direction that is finer than the resolution limit of the ultrasound transceiver system in said first direction. Each 3D resolution-enhanced image may have a resolution in a further direction, different from the first direction, that is finer than a resolution limit of the ultrasound transceiver system in the further direction. The further direction is preferably a lateral direction. Each 3D resolution-enhanced image preferably has a resolution in a second direction, different from the first direction and from the further direction, that is finer than a resolution limit of the ultrasound transceiver system in the second direction. In some embodiments, the resolution limit in the further direction may equal the resolution limit in the first direction, or may equal the resolution limit in the second direction. This may be the case, for example, when two orthogonal lateral axes have a common resolution limit.

The ultrasound imaging system may be arranged to generate said data representing a sequence of images over time. The input will then form part of an internal interface within the imaging system, between the ultrasound transceiver system and the processing subsystem. The ultrasound imaging system or the ultrasound transceiver system may comprise one or more ultrasound transducers for transmitting ultrasound signals into a living organism. The ultrasound transceiver system may comprise one or more ultrasound transducers for receiving reflected ultrasound signals from fluid that is flowing along a path within the living organism. It may comprise a processor or other means for generating the data representing the sequence of images over time from data representing received ultrasound signals—e.g., from analogue RF signals from one or more ultrasound transducers. This processor or other means may be part of the previously-described processing subsystem or may be separate from it. The ultrasound imaging system may comprise a handheld scanner unit containing one or more ultrasound transducers for transmitting and/or receiving ultrasound. The ultrasound imaging system may comprise an electronic display, such as an LCD monitor.

The data representing a sequence of images over time preferably comprises amplitude information. It may be obtained using conventional techniques. Speckle patterns occur normally in such images, due to constructive and destructive interference between scattered wave-fronts. Traditionally, however, speckle is considered to be unwanted noise. Some systems try to filter it out. The present invention, by contrast, positively exploits the speckle pattern to provide super-resolution imaging.

Speckle patterns have been used in the past to analyse the motion of tissue in an organism by tracking movement of the speckle pattern over time. However, such motion analysis is quite different from the present invention, which is concerned with the generation of super-resolution images of fluid paths. For example, the use of speckle patterns for visualising blood flows at standard imaging resolutions (i.e., not enhanced-resolution imaging) has been described in U.S. Pat. No. 6,277,075, in which processed speckle patterns are combined with conventional tissue images for display.

The data representing the sequence of images over time preferably comprises a set of values—preferably representing an array of pixel values. Each pixel may represent an amplitude value from the ultrasound transceiver system. The pixels may be rectangular (e.g., after a scan conversion step), but preferably have a shape determined by the geometry of the transceiver system—e.g., with each pixel being a parallelogram or being an annual sector. The image data may be derived from beamformed and complex-demodulated I/Q data samples, or the processing may be performed on real-valued RF data without complex demodulation. The received ultrasound signals may also be used to generate data related to frequency or phase. This may be used for Doppler-based processing of the image data.

The resolution of the resolution-enhanced images in the first or second direction may be the minimum or maximum or mean spacing between a pair of adjacent pixels. The direction and spacing may be given in an appropriate coordinate system, such as an inherent coordinate system of the transceiver system, or Cartesian coordinates. For at least one direction in the image data, the pixel spacing is preferably uniform.

The peak-sharpening is preferably applied to the data before any nonlinear compression (e.g., logarithm compression), dynamic-range adjustment, pixel-value quantisation, scan conversion, or other display-rendering processing operation is applied to the data, so that no amplitude information is lost at this stage. References to "pixels" and "images" herein should not be understood as implying that any such operations have necessarily already been applied to the data.

The image data preferably has, during at least some of the processing operations, a resolution (e.g., pixel density), in the first and/or second direction, that is finer than the resolution limit of the ultrasound transceiver system, used to generate the image data, in the respective direction, by a factor of two or more (e.g., by a factor of ten, twenty or more). In particular, the resolution-enhanced image data, after the peak-sharpening operation, preferably has a resolution (e.g., pixel spacing) that is two, ten, twenty or more times finer than the resolution limit of the ultrasound transceiver system.

Such oversampling in the image data may be achieved inherently by using a beam-former that outputs measurements at a higher spatial resolution than a diffraction-limiting element of the ultrasound transceiver system, for the transmitted ultrasound signals. However, in other embodiments the ultrasound imaging system may be configured to process the received image data (e.g., by resampling the image data) to generate additional interpolated pixels within the image data; this may, for instance, be done before the peak-sharpening operation is applied to the image data (in the processing subsystem), or as part of the peak-sharpening operation. Any suitable known interpolation method may be used. The additional pixels in the image data facilitate the generation of a super-resolution output image during the subsequent image-processing operations.

The sequence of images over time may have any appropriate frame rate—for example, equal to or between 100 Hz and 1,000 Hz, or more. The rate may depend on the typical velocities of the fluid that is being imaged. It may be determined by a user input. Similarly, the number of image frames in the in the sequence may depend on what is being imaged, and may be user-configurable.

The data representing the sequence of images over time is preferably filtered with a frame-to-frame high-pass filter, or clutter filter. This filtering is preferably performed by the processing subsystem, preferably before the peak-sharpening operation is applied to the image data. This filtering preferably attenuates contributions from matter in the living organism that is stationary or moving slowly (e.g., at less than a threshold speed in one or more directions) within the living organism, such as muscle, fat, etc., as well as the walls of any blood vessels. The filtering of the image data can reduce or remove stationary or slow-moving clutter which may otherwise impair the super-resolution imaging of the moving fluid. This is beneficial because the speckle pattern is typically relatively faint compared with the signal from some static reflectors in the living organism. Such filtering is particularly useful when a contrast agent is not being used.

Any conventional clutter filter may be used. The filtering may use frequency or phase information (e.g., Doppler-shift information) determined from one or more received ultrasound signals. In one set of embodiments, data representing one or more power-Doppler images is generated. Filtering pixel values that represent zero or little movement perpendicular to the imaging plane could potentially filter out useful data relating to fluid moving parallel to the imaging plane, so care must be taken to mitigate this. In the case of blood, the three-dimensional shape of the blood cells typically causes a non-zero Doppler response perpendicular to the direction of flow of the blood, and this effect can be used to avoid filtering out the signals from the blood, e.g. by adjusting the clutter filter so that it only attenuates signals from tissue moving at below the speed of this Doppler response.

In other embodiments, the filtering may comprise a high-pass temporal filtering of the image sequence, not based on Doppler-shift information—e.g., using frame-to-frame differential processing to remove slow-changing information from the sequence of images. Preferably, however, a more sophisticated clutter filtering approach is used additionally or instead.

The filter may be such that it attenuates signals from matter moving at below, but not above, a threshold speed. Such a threshold speed may be set explicitly (e.g., based on a value stored in a digital memory, which may be user-configurable), or it may be inherent in the filtering operation—e.g., based on an inbuilt or adaptive cut-off applied by a clutter filter. The threshold speed may apply to motion within the imaging plane, or to motion perpendicular to the imaging plane, or to any other directional component of velocity, or to actual speed in three dimensions, and may be absolute or relative to another point on the living organism, or to a component of the ultrasound transceiver system, such as a handheld scanner unit.

The peak-sharpening operation increases the effective resolution of the image data by generating output at a finer resolution than the resolution limit of the ultrasound transceiver system used to generate the image data. The peak-sharpening operation may calculate an output pixel value based on a plurality of input pixel values (e.g., acting on a multi-pixel input window), but in a preferred set of embodiments it acts on each pixel of the image data independently of any other pixels.

The peak-sharpening operation preferably comprises or consists of applying a non-linear function to pixel values (or amplitude values) in the (over-sampled) image data. It preferably amplifies extreme values (preferably relatively high values) within the image data more than it amplifies non-extreme values (preferably relatively low values).

The function may be a power function or polynomial function, e.g. $f(x)=a+b \cdot x^n$, preferably with a power, n, greater than one. The function may be an exponential function, e.g. $f(x)=a+b^x$, or comprise an exponential term, preferably with a base, b, greater than one. The first derivative of the function is preferably monotonically increasing over the range of pixel values that are present in the image data before the peak-sharpening operation is applied to the image data.

In some preferred embodiments, the peak-sharpening operation comprises applying an power function to the pixel intensity values—for example, replacing each pixel value with the eighth power of the pixel's original value ($y=x^8$). An eighth-power power function has been found to give particularly good results when imaging blood vessels. However, other exponents, such as two, four, six, ten, twelve, or more, or in the range two to twelve, may of course be used. Other non-linear functions may be used. For example, a function could be used that increases the value of those pixels that have an original value above a threshold level by more than it changes the value of those pixels having an original value below the threshold level (e.g., by scaling pixels above the threshold by a linear factor, while leaving pixels below the threshold unchanged).

In addition to the peak-sharpening operation, a normalising operation is preferably applied to the resolution-enhanced image data, preferably by the processing subsystem and preferably before the combining operation is applied to the (normalised) data. The normalising operation preferably reduces the variation in the magnitude of local peaks within an image frame of the image data (i.e., to reduce the difference between the largest local-maximum value and the smallest local-maximum value in each image). This is preferably carried out after the peak-sharpening operation—i.e., on the resolution-enhanced image data. In this way, relatively weak peaks are brightened relative to relatively strong peaks. This allows more peaks to contribute to the resulting output image.

The normalising operation preferably comprises scaling the values of pixels in the image data based on the values of the pixels in a neighbourhood (kernel) around each respective pixel. In a preferred set of embodiments, each pixel value in the resolution-enhanced image data is divided by the average (mean or median, optionally weighted according to a pattern of weights) of the pixel values in the resolution-enhanced image data in a neighbourhood of the pixel. The size or shape of the neighbourhood may be fixed. A pattern of weights may provide a scaling weight for each pixel in the neighbourhood. For example, weights representing a separable or radial two-dimensional Hamming window may be used.

The neighbourhood may have any appropriate shape, such as circular, but is preferably rectangular (e.g., square) for reasons of computational efficiency. It may have any appropriate size, but it is preferably substantially the same size, in at least one direction, as the resolution limit of the ultrasound transceiver system—e.g., having a maximum dimension (e.g. width) that is no less than a third or a half or three-quarters of the resolution limit, and/or that is no more than 125% or double or three times the resolution limit. Normalising the data using a kernel having approximately the same size as the resolution limit has been found to lead to particularly clear images of blood flow, once the subsequent combining operation has been applied to the data.

In some embodiments, the normalising operation may comprise temporal averaging of one or more pixel values across a plurality of image frames. For instance, the average value of a neighbourhood around a pixel may be averaged over a succession of two or more images, before scaling the pixel value by that average. This can help to prevent flickering in the image sequence; this is particularly desirable if a plurality of output images are to be generated and displayed as a video.

It is important to note that the peak-sharpening operation and the optional normalising operation are preferably applied directly to the raw amplitude data, rather than to data that has been log-compressed or quantised. They are therefore not directly equivalent to conventional image-processing operations that might be applied to scaled and quantised pixel data, such as bitmap images.

The combining operation preferably comprises, for each pixel in the output image, calculating an average (mean or median, optionally weighted according to a weighting function) of the values of that pixel across the sequence of resolution-enhanced images, or across a sub-sequence of the resolution-enhanced images. The value of the pixel in the output image may equal this average. Alternatively, one or more further operations may be applied, using this average value, to generate the data representing the output image. For example, the data may be log-compressed and/or dynamically range-adjusted and/or scaled up or down spatially and/or quantised for rendering on a display.

By using temporal averaging to superimpose a plurality of peak-sharpened speckle patterns over time, the path of the fluid becomes visible in the output image, in a similar way to how a long-exposure photograph of the night sky shows the path of the stars due to the Earth's rotation, or as a long-exposure photograph of a waterfall emphasises the path of the flow.

This superimposing effect may be enhanced for certain fluids, such as blood, which exhibit a relatively consistent speckle pattern from frame to frame when the fluid is flowing substantially parallel to the imaging plane. In this case, the combining operation will generate speckle trails in the output image, which can enhance the usefulness of the image by providing a qualitative indication of flow along the vessel. In some embodiments, a velocity analysis operation may be performed to determine a quantitative estimate for the speed or velocity of the fluid, based on tracking the movement of one or more elements in the speckle pattern over a plurality of frames. In other embodiments, velocity information may be determined based on Doppler frequency shift information. Regardless of how it is obtained, velocity information may be included in the output image—e.g., as a colour overlay.

Thermal noise may create a similar speckle pattern to that of the fluid, but typically with lower amplitude. Since the noise pattern is independent from frame to frame, temporal averaging will attenuate the noise pattern such that it can easily be distinguished from the fluid path in the output image.

Noise may be further reduced by merging the output image with a conventional power Doppler image—for example, by taking the mean value of each pixel across the two images. This is because noise has lower values in the power Doppler image.

In some embodiments, a succession of output image frames may be generated. These may be displayed as a video, e.g., on a display screen. In situations where the speckle pattern is somewhat consistent from frame to frame, the combining operation may be such that, for each output image frame, one image from within the sequence of resolution-enhanced images which are used to generate the output image frame is given a higher weight than any of the other images in the sequence. Preferably this image has the same position within the sequence, for each output image frame (e.g., it is always the middle image of the sequence of resolution-enhanced images). In this way, a clear view of the speckle pattern is superimposed on the blurred rolling temporal average of the speckle pattern, in each frame of the video. The blurred pattern provides an accurate indication of the shape of the vessel in the video, while the succession of clear views of the speckle pattern give an indication of the movement of the fluid along the vessel to the person viewing the video. This has been found to provide a particularly useful way of viewing vessels to clinicians.

While a filtering operation, peak-sharpening operation, normalising operation and combining operation have been described as separate operations, it will be appreciated that a single algorithm, function or processing block may perform two or more of these operations. Some mathematical functions may conflate two or more of these operations into a single operation. While these operations have been described as being performed in a particular order, for ease of understanding, it will be appreciated that they may, where appropriate, in practice be carried out in a different order, or two or more may be carried out in parallel.

The ultrasound imaging system, and its processing subsystem, may comprise one or more processors, DSPs, ASICs, volatile memory, non-volatile memory, inputs, outputs, etc. as will be appreciated by one skilled in the art. Some or all of the operations may be carried out by, or under the control of, software stored in a memory and executing on one or more processors in the processing subsystem. The ultrasound imaging system may be a single unit or it may be distributed—e.g. with one or more operations being performed remotely from the living organism, such as on a remote server. The operations need not necessarily be performed close in time to one another. In particular, the ultrasound signals may be acquired at a first period in time, and then processed at a later period of time, which may be days apart.

Features of any aspect or embodiment described herein may, wherever appropriate, be applied to any other aspect or embodiment described herein. Where reference is made to different embodiments or sets of embodiments, it should be understood that these are not necessarily distinct but may overlap.

BRIEF DESCRIPTION OF THE FIGURES

Certain preferred embodiments of the invention will now be described, by way of example only, with reference to the accompanying drawings, in which.

DETAILED DESCRIPTION OF THE PREFERRED EMBODIMENTS

Figure 1:
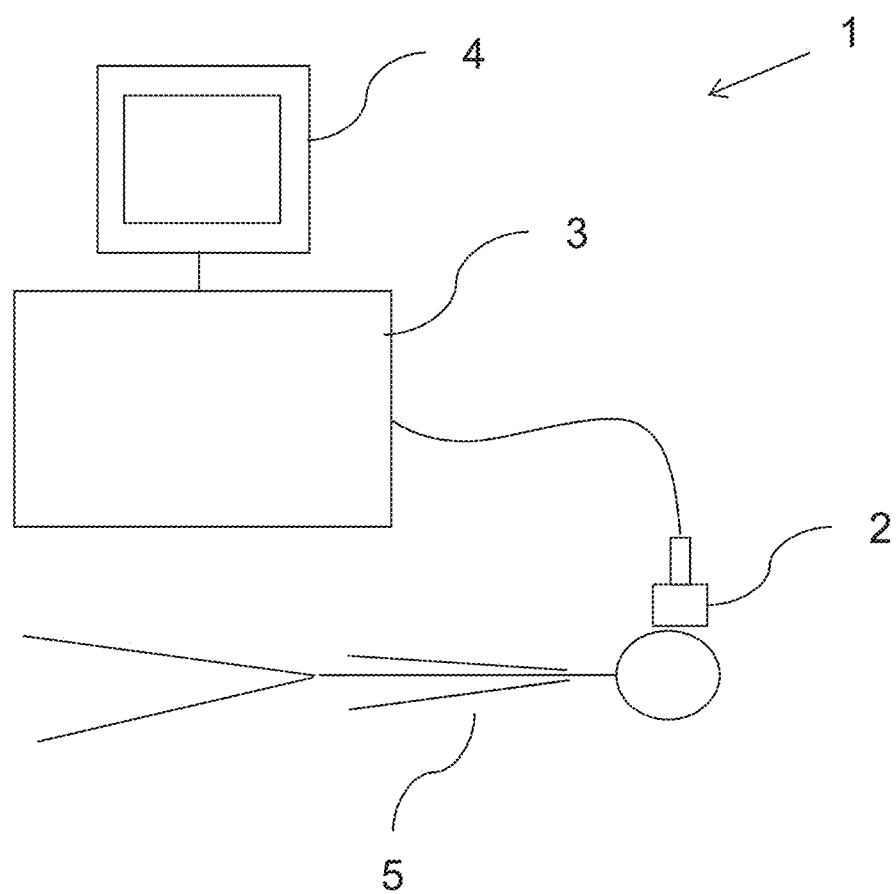
FIG. 1 is a figurative drawing of a scanning system embodying the invention.

FIG. 1 shows a super-resolution ultrasound scanning system 1. It includes a handheld linear-array ultrasound probe 2, a processing unit 3, and a display 4. The ultrasound probe 2 contains an array of ultrasound transducers for transmitting signals (e.g., a series of pulses) and for receiving reflections of the signals, under the control of the processing unit 3. Beamforming can be used to steer the transmitted signals in a particular direction and/or to receive reflections from a particular direction.

The ultrasound scanning system 1 is used by an operator, such as sonographer or physician, to see inside the body of a patient 5. In particular, the system 1 may be used to visualise the shape of small blood vessels, such as cerebral microvessels, in the patient 5 on the display 4, although it is not limited just to this application.

While currently-preferred embodiments use an ultrasound probe 2 having a one-dimensional array of transducers, which supports beamforming within a thin "slice" through the patient 5, other embodiments may use a two-dimensional transducer array which can capture three-dimensional data. Such a probe could be used to generate image data in a 3D volume.

The processing unit 3 contains a processor, memory, and other components (not shown) for controlling the transmission of signals from the probe 2, and for processing the received signals. The processing unit 3 may be conventional, apart from the software that it executes in order to implement features embodying the present invention. However, it may have non-standard hardware in some embodiments. The processing unit 3 can comprise any one of more of: a central processing unit, a graphics processing unit, a microcontroller, an ASIC and an FPGA. It may execute software instructions stored in a memory. In some embodiments, a remote server (not shown) may be connected to the processing unit 3 by a network and may be used to perform at least some of the described processing operations.

Figure 2:
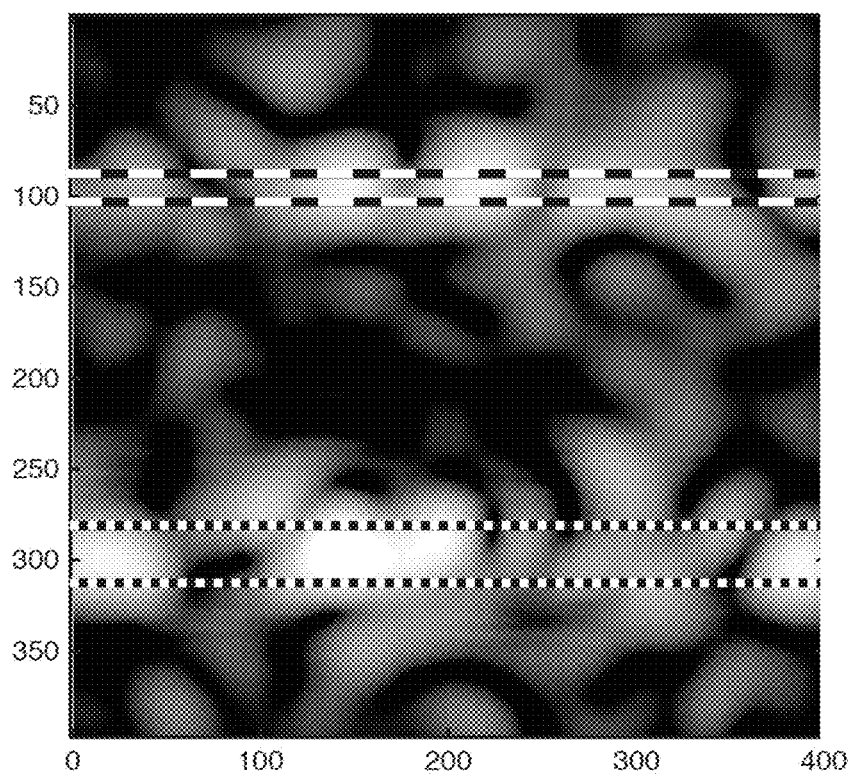
FIG. 2 is a conventional power Doppler image.

FIG. 2 shows a portion of a power Doppler image of a human patient. This image has been generated using conventional techniques. High-pass clutter filtering has been applied to reduce contributions from stationary or slow-moving tissue. The data has been log-compressed in order to generate this image. Two blood vessels, running horizontally across the image, have been highlighted on the figure with two pairs of dashed lines. Speckle patterns from the blood can be seen in the image; however, due to the resolution limits of the scanning system 1, these patterns are not confined within the blood vessel walls, but extend beyond them. It is impossible, from this image, to determine the precise boundaries of the blood vessels.

Figure 3:
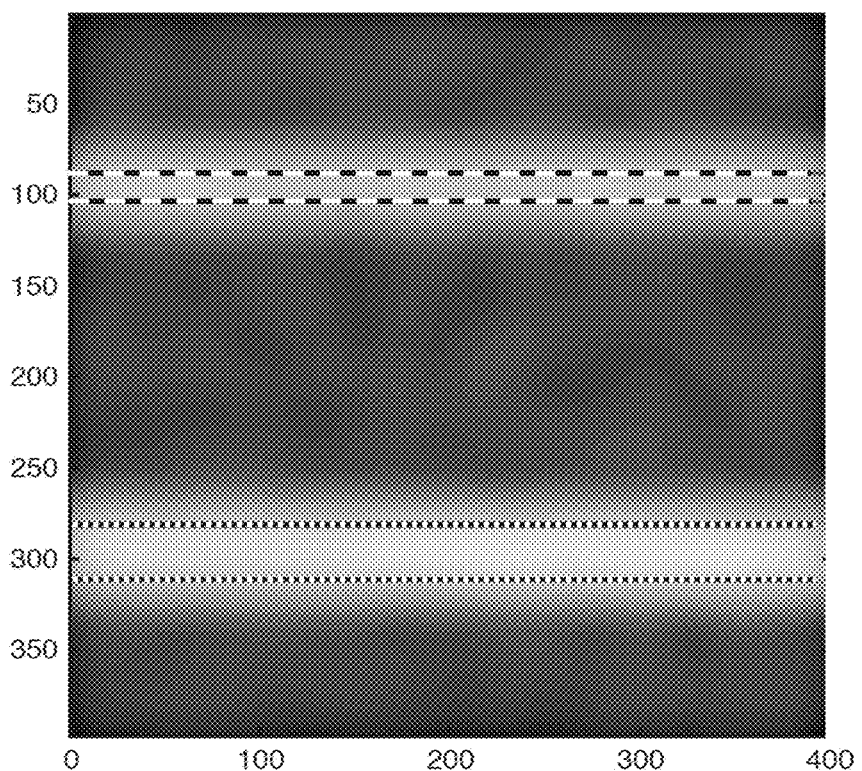
FIG. 3 is a temporally-averaged sequence of conventional power Doppler images.

FIG. 3 shows the result of (i) applying temporal averaging to a succession of such power-Doppler images and (ii) combining this average with a B-mode image, both of which actions help to suppress noise. While this helps to make the shape of the blood vessels more apparent, the boundaries of the blood vessels are still fuzzy and imprecise.

By contrast, the super-resolution ultrasound scanning system 1 applies the following processing steps (potentially, but not necessarily, in this order) to a sequence of image frames acquired using the probe 2:

clutter filtering;
over-sampling;
peak-sharpening;
normalising;
temporal averaging; and
logarithmic compression.

A known clutter filtering technique is used to attenuate contributions from slow-moving or stationary tissue. This can substantially reduce signals from tissue such as muscle and bone, which will typically be much stronger than the reflections from fluid such as blood. It can also allow for unintentional movement between the handheld probe 2 and the patient 5 which will typically be slower than the speed of the blood flow. The clutter filter may use Doppler-shift information to filter the amplitude data, e.g. as is known when generating power Doppler images.

Each image frame will typically start off having a pixel resolution approximately equal to the resolution limit of the scanning system 1. In an over-sampling step, each image frame is resampled to increase the pixel density—for example, by replacing each rectangular pixel in the image data with a grid of smaller rectangular pixels (e.g., with 400 pixels in a 20×20 grid). The new pixel values are preferably interpolated from the original image data (e.g., using bicubic interpolation).

The peak-sharpening involves applying a nonlinear function to each pixel value in the (resampled) image data. In some embodiments, a power-law function such as $x^8$ or $x^{12}$ is used. This has the effect of "sharpening" the local peaks in the random speckle patterns in the image data and increasing the effective resolution of the image data beyond the resolution limits of the scanning system 1.

The peak-sharpening may result in a large variation in the heights of different local peaks in the speckle patterns. In order to reduce the large variation, each image pixel is normalized by the average (e.g. mean) value in a local spatial and temporal area around each pixel.

Figure 4:
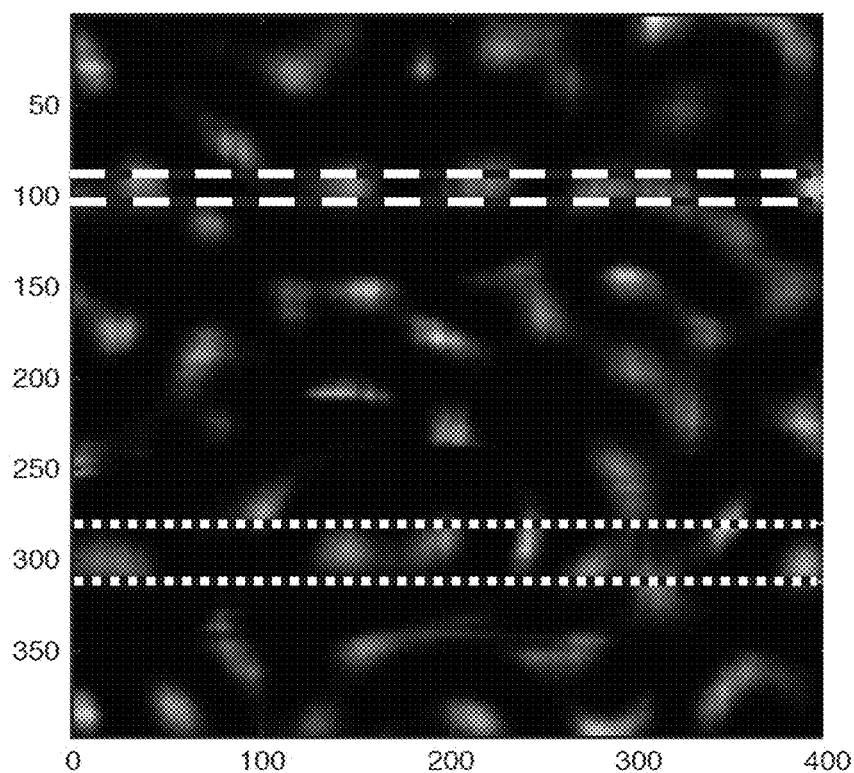
FIG. 4 is a resolution-enhanced image generated by a scanning system embodying the invention.

FIG. 4 shows the result of applying these clutter-filtering, over-sampling, peak-sharpening and normalising steps to the same data from which the power Doppler image of FIG. 3 was generated. The resulting data has then been log compressed in order to generate FIG. 4, The enhanced speckle pattern from the blood is now confined within the walls of the vessels, whose true locations are represented by the two pairs of dashed lines.

Figure 5:
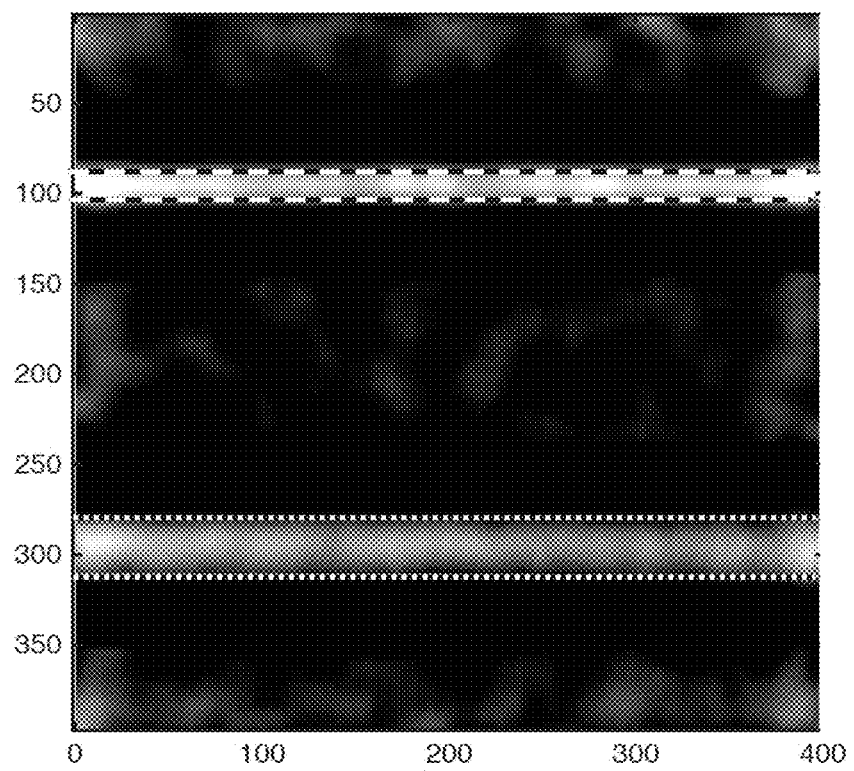
FIG. 5 is a temporally-averaged sequence of resolution-enhanced images generated by a scanning system embodying the invention.

FIG. 5 shows the shows the result of (i) applying temporal averaging to a succession of one hundred such super-resolution image frames and (ii) combining this average with a power Doppler image by taking a linear combination after log compression. These actions help to suppress noise, such as thermal noise, and enhance the visibility of the blood vessels by "filling" the interior of the vessel with superimposed enhanced speckle patterns. This creates a smooth white/grey appearance to the vessel, with substantial improvement in spatial resolution compared with the output image of FIG. 3.

The final output image may be processed for display (e.g., by log compression and dynamic-range adjustments) and shown on the display 4.

This super-resolution technique can also be combined with other techniques to quantify blood motion velocity, e.g. Doppler frequency shift, or velocity vector estimation based on speckle tracking.

The blood motion may be visualised dynamically on the display 4 by as a video by combining a succession of super-resolution image frames with temporal filtering with a succession of super-resolution image frames without the temporal filtering. In this way, each video frame contains both the "filled" shape of the interior of the blood vessel, which will remain fairly constant over time, and a single instance of the speckle pattern, which will change from one frame to the next, giving a subjective indication of the speed and direction of the blood flowing along the vessel (within the image plane).

Figure 6:
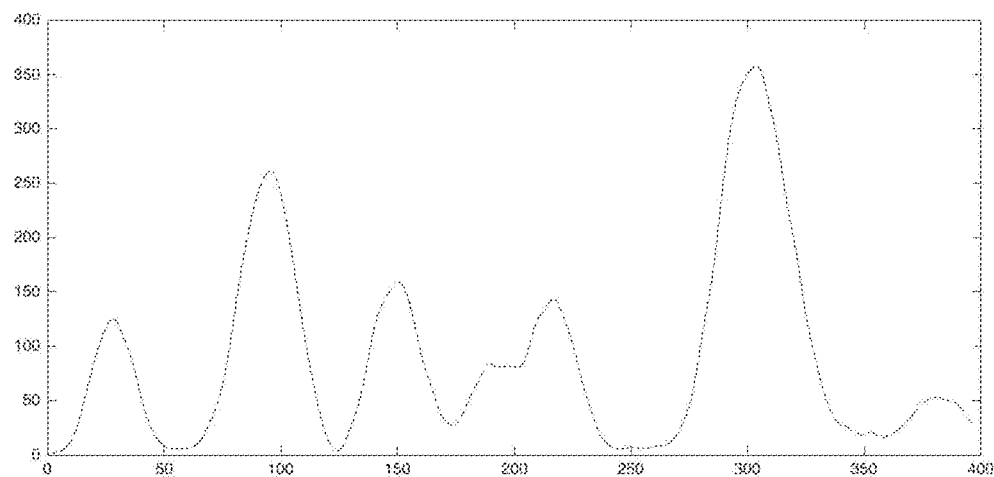
FIG. 6 is a graph of amplitude along one dimension of a power Doppler image.
Figure 7:
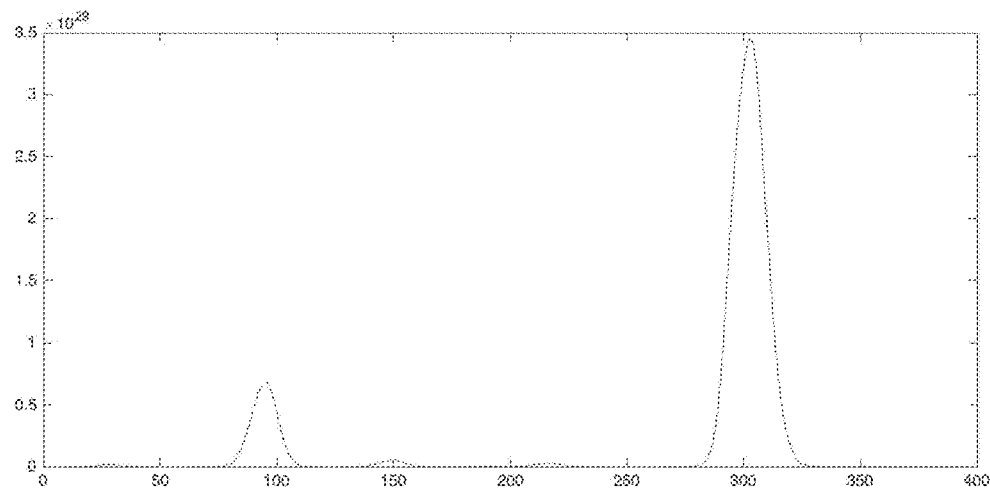
FIG. 7 is a graph of amplitude after resolution enhancement.
Figure 8:
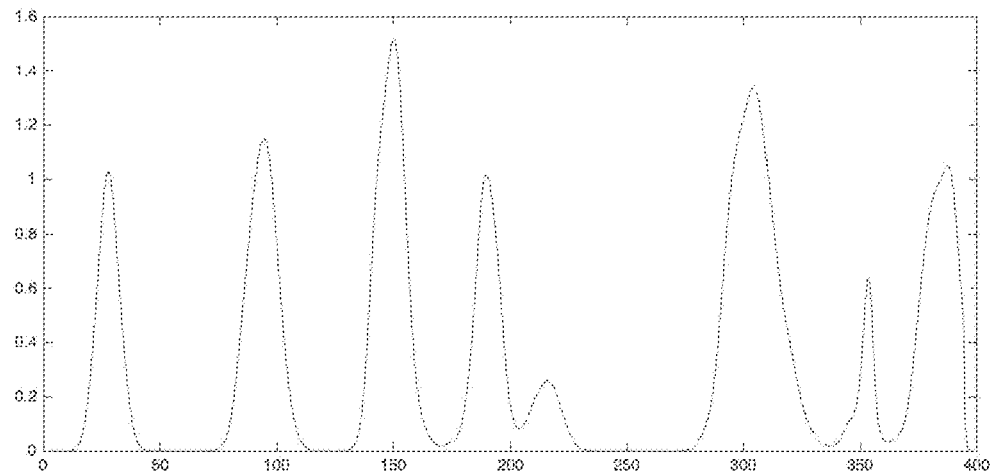
FIG. 8 is a graph of amplitude after normalisation.

FIGS. 6, 7 and 8 each show amplitude (vertical axes) against distance (horizontal axes) along an exemplary line through a two-dimensional image data set.

FIG. 6 shows the amplitude within an over-sampled standard power Doppler image (without log compression).

FIG. 7 shows the result, along the same line, of applying an $x^{12}$ peak-sharpening operation to the over-sampled two-dimensional image data set. The linear vertical axis has been rescaled to accommodate the larger values that are now present in the data. It can be seen that the peaks in the input power-Doppler image data have become sharper, but only the largest two peaks are easily visible in the sharpened data (the other peaks are still present in the data set, but are not visible on the graph).

Figure 9:
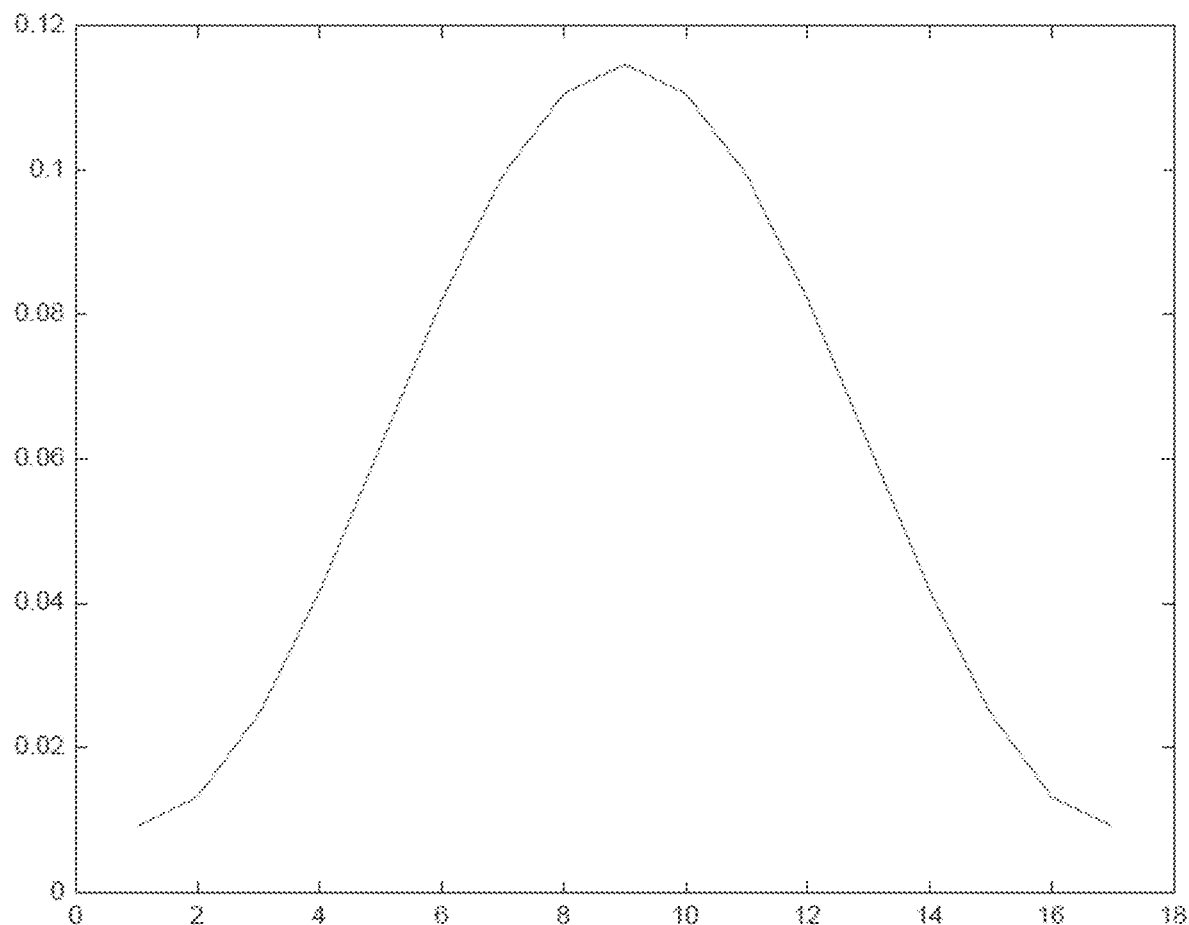
FIG. 9 is a plot of a Hamming window.

FIG. 8 shows the result, along the same line, of normalising the peak-sharpened data, by applying a 17-point Hamming window function to the data in a two-dimensional convolution operation. Such a Hamming window function (in one dimension) is shown in FIG. 9. The linear vertical axes has rescaled again, as the values in the data set are now much smaller. It can be seen that this operation has the effect of de-emphasising the two largest peaks from the peak-sharpened data, relative to other peaks in the data. The resulting peaks are narrower than they were in the original power-Doppler image. This means that there is less overspill of the speckle pattern beyond the walls of the blood vessel. When temporal averaging is applied to a sequence of such image data sets, the resulting superimposed speckle patterns will yield a super-resolution image of the interior of the blood vessel.

Figure 10:
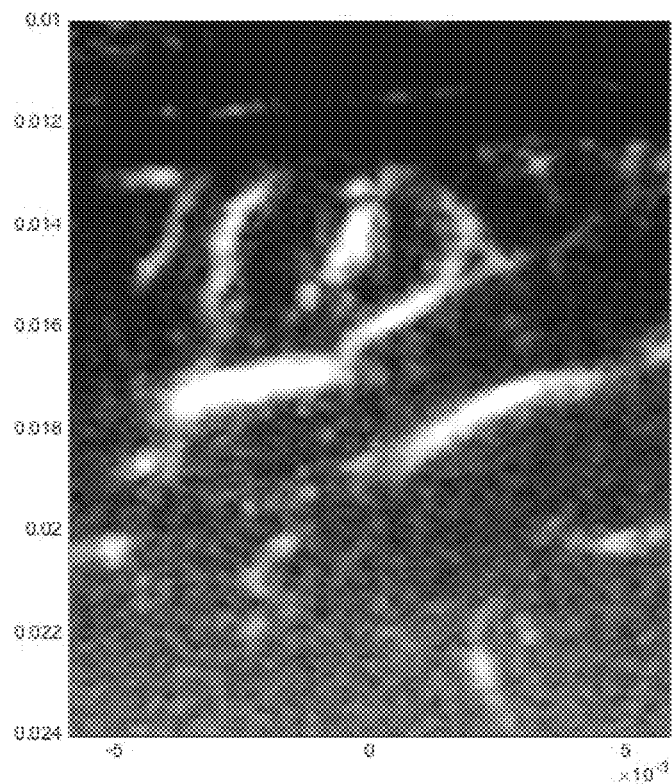
FIG. 10 is a conventional power Doppler image of a human thyroid gland.

FIG. 10 shows a conventional power Doppler image of a human thyroid gland, generated from a data set. The blurred shape of blood flow within the thyroid gland is visible, but the patterns are relatively indistinct and do not give a clear indication of the boundaries of the blood vessels.

Figure 11:
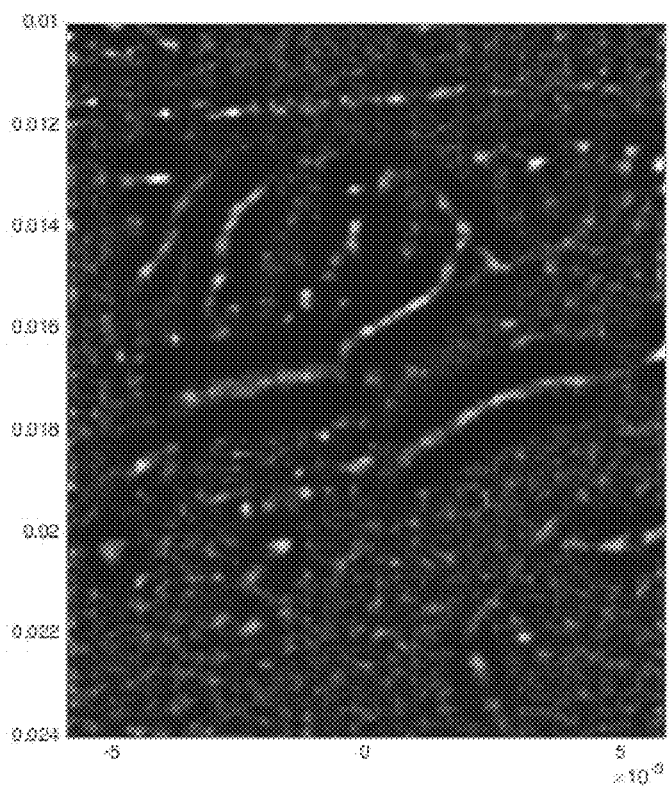
FIG. 11 is a super-resolution image of the human thyroid gland.

FIG. 11 shows the result of applying the super-resolution processing steps described above to the same data set as in FIG. 10. The same blood vessels are now much narrower and clearer. Their locations can be identified more precisely.

Figure 12:
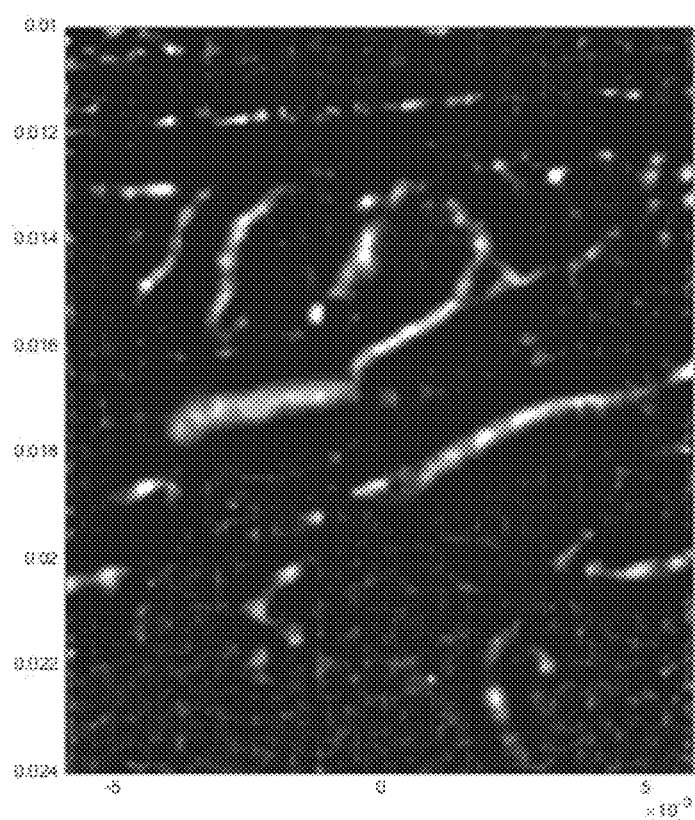
FIG. 12 is noise-suppressed super-resolution image of the human thyroid gland.

FIG. 12 shows the result of applying noise suppression to the image data of FIG. 11, by combining the super-resolution image data with the conventional power Doppler image of FIG. 10. Although there is some reduction in the clarity of the outline of the blood vessels, this is compensated for by a reduction in noise outside the blood vessels, which may be a worthwhile trade-off in some clinical settings.

Figure 13:
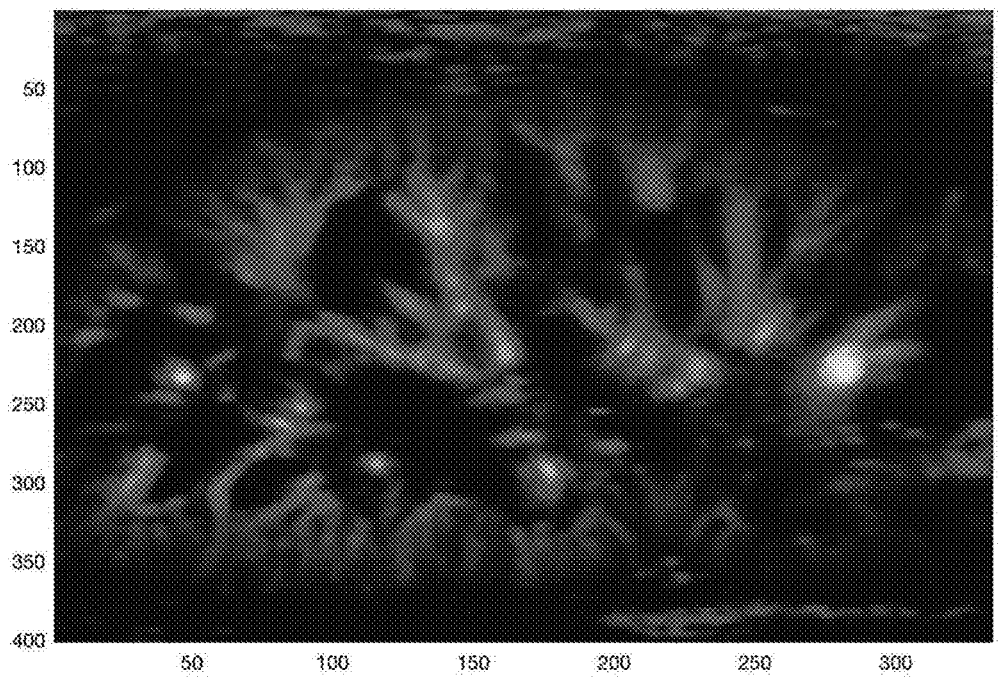
FIG. 13 is an image of a vasculature in a kidney taken using a conventional Doppler scanning system.

FIG. 13 shows a conventional power Doppler image of a vasculature in a kidney.

Figure 14:
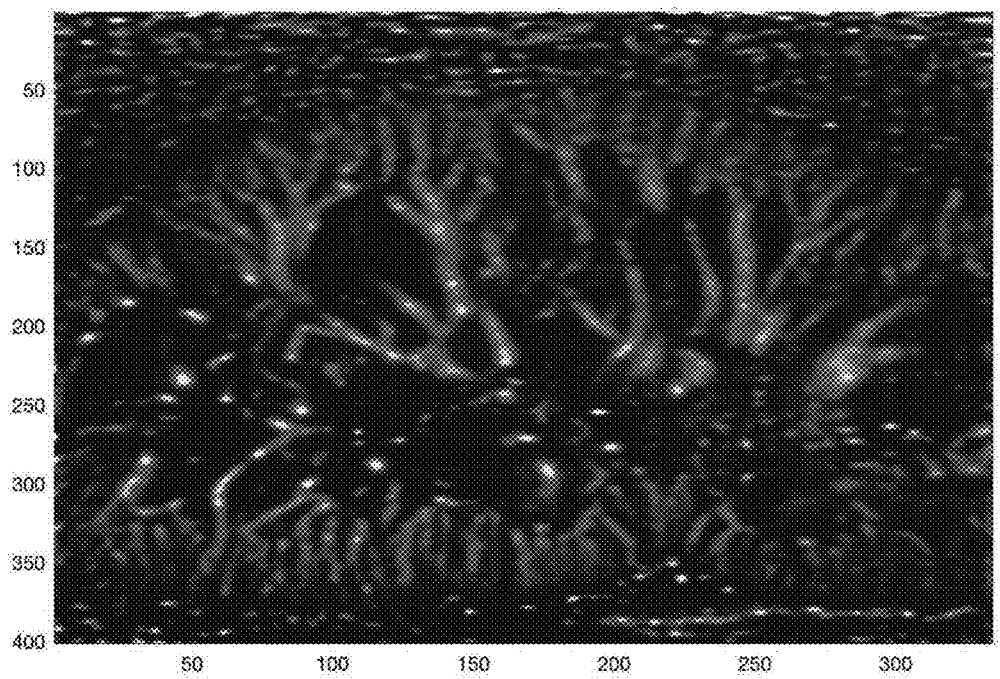
FIG. 14 is an image of a vasculature in a kidney taken using a super-resolution scanning system embodying the invention.

FIG. 14 shows a super-resolution power Doppler image of a vasculature in a kidney resulting from use of the processing steps described herein.

The additional clarity and precision provided by embodiments of the present invention, as demonstrated in FIGS. 11 and 12, when compared with FIG. 10, as well as in FIG. 14 compared to FIG. 13, is readily apparent.

The invention claimed is:

1. An ultrasound imaging method comprising:
transmitting ultrasound signals into a living organism;
receiving reflected ultrasound signals from fluid that is flowing along a path within the living organism with an ultrasound transceiver system that has a resolution limit in a first direction;
using the received ultrasound signals to generate data representing a sequence of images over time, each image including a speckle pattern arising from interference within the ultrasound signals reflected from the fluid that is flowing along the path;
applying a peak-sharpening operation to the image data, to generate data representing a sequence of resolution-enhanced images, each resolution-enhanced image having a resolution in said first direction that is finer than the resolution limit of the ultrasound transceiver system in said first direction, and including a respective peak-sharpened speckle pattern; and
applying a combining operation to the data representing the sequence of resolution-enhanced images to generate data representing an output image in which the path of the fluid is represented by a superimposition of the peak-sharpened speckle patterns from the sequence of resolution-enhanced images.

2. The ultrasound imaging method as claimed in claim 1, wherein the fluid comprises blood.

3. The ultrasound imaging method as claimed in claim 1, wherein the peak-sharpening operation comprises applying a non-linear function to pixel values in the image data, wherein the first derivative of the non-linear function is monotonically increasing over the range of pixel values that are present in the image data before the peak-sharpening operation is applied to the image data.

4. The ultrasound imaging method as claimed in claim 1, comprising generating data representing a succession of output images, and displaying the succession of output images as a video.

5. An ultrasound imaging system comprising:
an input for receiving data from an ultrasound transceiver system, the data representing a sequence of images over time having a maximum resolution in a first direction, each image including a speckle pattern arising from interference within ultrasound signals reflected from fluid that is flowing along a path within a living organism; and
a processing subsystem configured to:
apply a peak-sharpening operation to the image data, to generate data representing a sequence of resolution-enhanced images, each resolution-enhanced image having a resolution in said first direction that is finer than said maximum resolution in said first direction, and including a respective peak-sharpened speckle-pattern; and
apply a combining operation to the data representing the sequence of resolution-enhanced images to generate data representing an output image in which the fluid path is represented by a superimposition of the peak-sharpened speckle-patterns from the sequence of resolution-enhanced images.

6. The ultrasound imaging system as claimed in claim 5, further comprising an ultrasound transceiver system, having a resolution limit in said first direction equal to the maximum resolution, for a particular set of transmitted ultrasound signals, and arranged to generate said data representing a sequence of images over time.

7. The ultrasound imaging system as claimed in claim 5, wherein the processing subsystem is further configured to resample the received data representing a sequence of images over time, to generate additional interpolated pixels within the image data.

8. The ultrasound imaging system as claimed in claim 5, wherein the processing subsystem is further configured to filter the received data representing a sequence of images with a clutter filter, wherein the clutter filter is arranged to use frequency or phase information determined from one or more received ultrasound signals to attenuate contributions from matter in the living organism that is stationary or moving at less than a threshold speed in one or more directions.

9. The ultrasound imaging system as claimed in claim 5, wherein each resolution-enhanced image has a pixel spacing that is finer than the diffraction limit of the ultrasound transceiver system by a factor of at least two.

10. The ultrasound imaging system as claimed in claim 5, wherein the received data representing the sequence of images over time has a maximum resolution in a second direction, different from the first direction, and wherein each resolution-enhanced image has a resolution in said second direction that is finer than said maximum resolution in the second direction.

11. The ultrasound imaging system as claimed in claim 5, wherein the peak-sharpening operation comprises applying a non-linear function to pixel values in the image data.

12. The ultrasound imaging system as claimed in claim 11, wherein the first derivative of the non-linear function is monotonically increasing over the range of pixel values that are present in the image data before the peak-sharpening operation is applied to the image data.

13. The ultrasound imaging system as claimed in claim 11, wherein the peak-sharpening operation comprises applying a power function having an exponent greater than one to each pixel value in the image data, or applying an exponential function having a base greater than one to each pixel value in the image data.

14. The ultrasound imaging system as claimed in claim 5, wherein the processing subsystem is configured to apply a normalising operation to the resolution-enhanced image data to reduce the variation in the magnitude of local peaks within each resolution-enhanced image.

15. The ultrasound imaging system as claimed in claim 14, wherein the normalising operation comprises scaling the value of each pixel in the resolution-enhanced image data based on the values of pixels in a neighbourhood around the respective pixel in the resolution-enhanced image data.

16. The ultrasound imaging system as claimed in claim 14, wherein the normalising operation comprises temporal averaging of one or more pixel values across a plurality of images in the resolution-enhanced image data.

17. The ultrasound imaging system as claimed in claim 5, wherein the combining operation comprises, for each pixel in the output image, calculating an average of the values of that pixel across the sequence of resolution-enhanced images.

18. The ultrasound imaging system as claimed in claim 5, comprising a display screen and wherein the processing subsystem is configured to generate data representing a succession of output images, and to display the output images as a video on the display screen.

19. The ultrasound imaging system as claimed in claim 18, wherein the combining operation used to generate each output image comprises calculating a weighted average of the sequence of resolution-enhanced images, with a higher weight being given to one image in the sequence than any of the weights that are given to the other images in the sequence.

20. The ultrasound imaging system as claimed in claim 5, wherein the system is configured to reduce noise by merging the output image with a power Doppler image.

21. An ultrasound imaging system comprising:
an input for receiving data from an ultrasound transceiver system, the data representing a sequence of images over time, each image having a first resolution in a first direction and including a speckle pattern arising from interference within ultrasound signals reflected from fluid that is flowing along a path within a living organism; and
a processing subsystem configured to:
apply a peak-sharpening operation to the image data, to generate data representing a sequence of resolution-enhanced images, each resolution-enhanced image having a second resolution in said first direction that is finer than said first resolution, and including a respective peak-sharpened speckle-pattern; and
apply a combining operation to the data representing the sequence of resolution-enhanced images to generate data representing an output image in which the fluid path is represented by a superimposition of the peak-sharpened speckle-patterns from the sequence of resolution-enhanced images.

* * * * *